Dec. 25, 1962 M. D. RAVINE Plant Pat. 2,205
ROSE PLANT
Filed Feb. 1, 1962
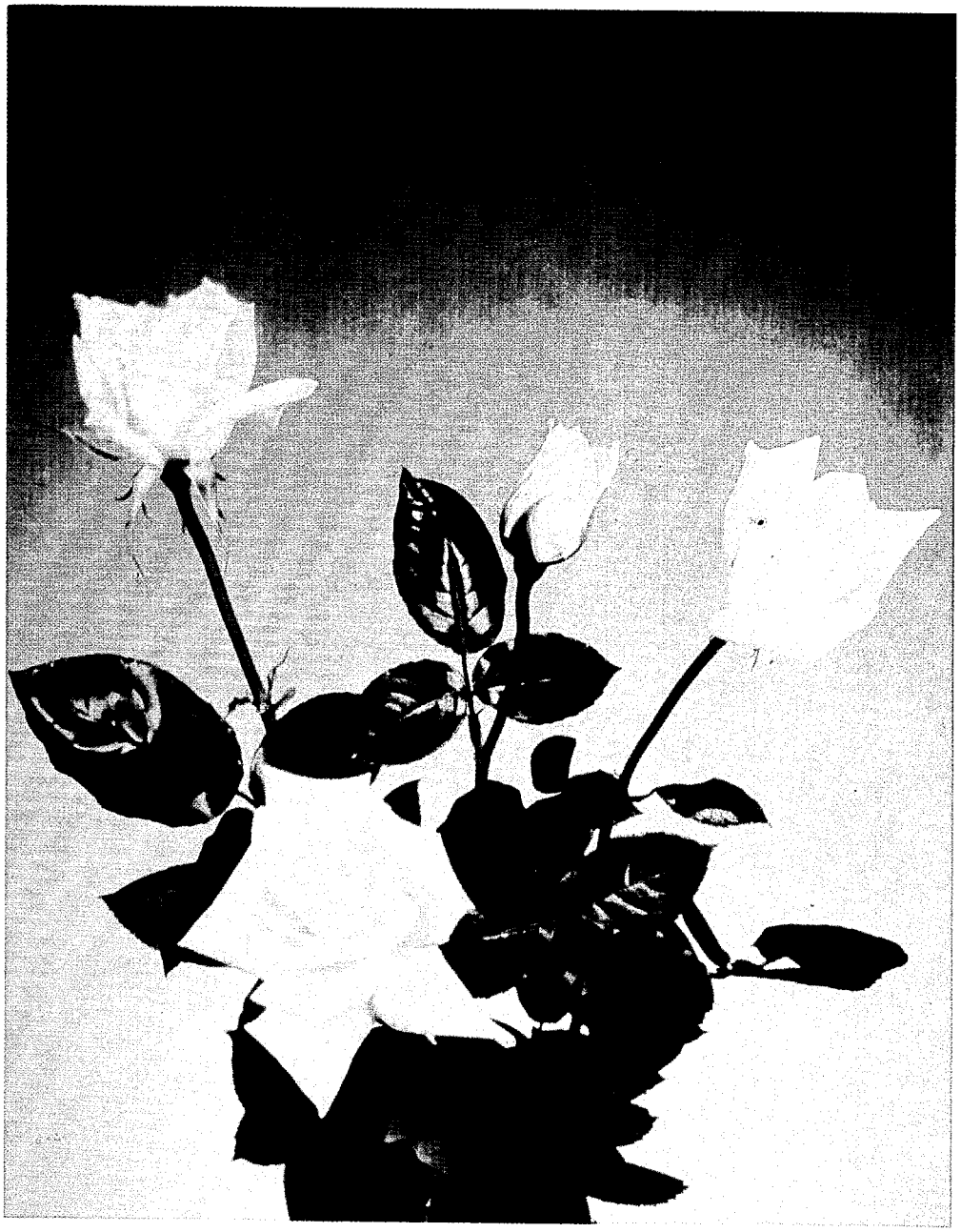
INVENTOR
Marion Domonic Ravine
BY Robb & Robb
ATTORNEYS United States Patent Office Plant Pat. 2,205
Patented Dec. 25, 1962

2,205
ROSE PLANT

Marion Domonic Ravine, New Philadelphia, Ohio, assignor to Endres Floral Company, Inc., New Philadelphia, Ohio, a corporation of Ohio Filed Feb. 1, 1962, Ser. No. 170,528
1 Claim. (Cl. 47—61)

The present invention relates to a new and distinct variety of rose plant which was discovered by me as a sport of the variety named "Golden Rapture" (unpatented).

At the time of my discovery aforementioned, I was employed by my assignee in the capacity of its chief rose grower, and in such capacity, I was engaged in growing plants of the variety "Golden Rapture" on the property of my assignee at New Philadelphia, Ohio. During my normal daily operations of tending these plantings, my attention was attracted to one plant amongst the "Golden Rapture" plants which bore flowers of a much deeper golden yellow color, with the flowers in the bud stage having copper tints extending from the tip of the bud for approximately one-third of its length. The foliage of this plant also appeared to be much darker and more waxy than the normal foliage of "Golden Rapture," with the leaves being a compound of seven leaflets, as distinguished from the compound arrangement of only five leaflets in the leaves of "Golden Rapture."

Upon close examination of this particular plant, I found that it had sported, and I thereupon took steps to preserve the sport, keep it under observation, and to later asexually reproduce the same. My observations of the original sport and of the asexually reproduced progeny thereof fully confirmed the distinctions between the sport and its parent, "Golden Rapture," as well as established the presence of other improved features. The following combination of outstanding characteristics of the new sport represent a unique, distinctive, and commercially important combination in roses of the yellow color range, and differentiates my new variety from its parent, as well as from all other varieties of which I am aware:

(1) Clean and healthy foliage;

(2) Much better resistance to fungi diseases, including both mildew and blackspot, as evidenced by freedom from these diseases while growing under the same conditions and in the same locality with other yellow varieties which became infected;

(3) Pointed flower buds of Deep Canary Yellow color, with the upper one-third of the bud being copper-tinted, or almost Oxblood Red as the calyx breaks, said copper and red tones gradually disappearing as the flower develops from a tight bud to a partly open bud, and thereafter holding its true Deep Canary Yellow color, regardless of the weather, throughout the life of the flowers until the petals fall; and (4) Good lasting qualities of the flowers both on the bush and as cut flowers.

Asexual reproduction of my new variety by own-root cuttings and by grafting, as performed at New Philadelphia, Ohio, and also by budding as performed at Carlton, Oregon, shows that the foregoing characteristics and distinctions come true to form and are established and transmitted through succeeding propagations.

The accompanying drawing shows typical specimens of the flowers and foliage of my new variety in different stages of development, and as depicted in color as nearly true as it is reasonably possible to make the same in a color illustration of this character.

The following is a detailed description of my new variety, with color terminology in accordance with the Horticultural Colour Chart issued by the British Colour Council, except where general color terms of ordinary dictionary significance are obvious:

Type: Hardy; bush; both greenhouse and outdoor; sport; for cut flowers and for garden decoration.
Class: Hybrid tea.
Parentage: Sport of "Golden Rapture."
Propagation: Holds its distinguishing characteristics through succeeding propagations by own-root cuttings, grating and budding.

*Flower*

Locality where grown and observed: New Philadelphia, Ohio, and Carlton, Oregon.
Continuity: Continuous.
Fragrance: Moderate. Nature—spicy.
Flowers borne: Singly to stem; on strong, medium long stems.
Quantity of bloom: Free and abundant, both outdoors and in greenhouse.
Bud:
*Peduncle.*—Short; heavy; erect; stiff; almost smooth; with few copper colored prickles. Color—dark green.
*Before calyx breaks.*—Size—large. Form—long; pointed; without foliaceous appendages on the surface of the bud; without foliaceous parts extending beyond the tip of the bud. Color—Spinach Green, Plate 0960/1.
*As calyx breaks.*—Color—golden yellow, with upper one-third copper-toned.
*As first petal opens.*—Size—large. Form—globular. Color: outside—Canary Yellow, Plate 2/2; inside—Canary Yellow, Plate 2/1.
*Opening.*—Opens up well; is retarded by cold and accelerated by heat.
Bloom:
*Size (when fully open).*—Large. Average size when fully expanded—from 5 inches to 6 inches.
*Petalage.*—Double (stamens not hidden); from 28 to 32 petals; arranged regularly.
*Form.*—Full and high-centered at first but becoming open and cupped; petals being at first loosely rolled outward, but later becoming very loosely rolled outward at maturity.
Petals:
*Texture.*—Thick; leathery.
*Appearance.*—Inside—velvety. Outside—satiny.
*Shape.*—Outside—oval; scalloped; with 2 notches. Intermediate—oval; scalloped; with 2 notches. Inside—round; scalloped; with 2 notches.

This description of a newly opened flower was made from a rose grown in a greenhouse during the month of August at New Philadelphia, Ohio:

*Color.*—Outer petal: outside surface—Canary Yellow, Plate 2/2, with the upper third of petal copper-tone; inside surface—Canary Yellow, Plate 2/1, with the upper third of petal copper-tone. Intermediate: outside surface—Canary Yellow, Plate 2/2, with the upper third of petal copper-tone; inside surface—Canary Yellow, Plate 2/1, with the upper third of petal copper-tone. Inner petal: outside surface—Canary Yellow, Plate 2/2, with the upper third of petal copper-tone; inside surface—Canary Yellow, Plate 2/1, with the upper third of petal copper-tone.

This description was made from a rose that was open for three days in a greenhouse during the month of August at New Philadelphia, Ohio:

*Color.*—Outer petal: outside surface—Canary Yellow, Plate 2/2; inside surface—Canary Yellow, Plate 2/1. Inner petal: outside surface—Canary Yellow, Plate 2/2. Inside surface—Canary Yellow, Plate 2/1.

*General color effect.*—Newly opened flower — golden yellow, with upper one-third of petals copper-toned. Three days open—entirely golden or Canary Yellow.

*Behavior.*—Holds color until petals fall off.

*Flower longevity.*—On bush in garden—from 8 to 10 days during August. Cut roses grown outdoors and kept at living room temperature—from 8 to 10 days during August. Cut roses grown in greenhouse and kept at living-room temperature—from 8 to 10 days during August.

*Reproductive Organs*

Stamens: Many; arranged regularly about pistils. Color—Oxblood Red, Plate 00823/3.

Filaments: Long; many; with anthers.

Anthers: Large; all open at once. Color—Reddish.

Pollen: Abundant. Color—gold.

Pistils: Many.

Styles: Uneven; short; medium caliper; bunched.

Stigma: Color—yellow.

Ovaries: All enclosed in calyx.

Hips: Globular; with conspicuous neck; smooth; thick walls. Color—green at first, but becoming scarlet.

Sepals: Falling soon; long; spear-shaped; curled. Color—Spinach Green, Plate 0960/2 at first, but becoming brown.

Seeds: Many; medium size. Color—light brown.

*Plant*

Foliage:

*Leaves.*—Compound of 7 leaflets; abundant; medium large; moderately heavy; glossy.

*Leaflets.*—Shape—ovate base, with cordate tip. Margin—simply serrate.

*Color.*—Mature: upper surface—dark green; under surface—normal green. Young: upper surface—moderately red; under surface—light red.

*Rachis (the supporting stem of the compound leaf).*—Medium heavy. Upper side—grooved. Under side—moderately thorny.

*Stipules.*—Long; narrow; with long points turning out at an angle less than 45°.

*Disease resistance.*—Very good resistance to fungi diseases, including mildew and blackspot, as determined by comparison with other varieties grown under comparable cultural conditions at New Philadelphia, Ohio.

Growth:

*Habit.*—Upright; much branched.

*Growth.*—Vigorous.

*Canes.*—Medium heavy.

*Main stems.*—Color—green. Thorns—several; medium length; hooked downward about 80°; with long, narrow base. Prickles—few; color—copper. Hairs—none.

*Branches.*—Color—green. Thorns—several; medium length; hooked downward about 80°; with long, narrow base. Prickles — few; color — copper. Hairs—none.

*New shoots.* — Color — copper. Thorns—several; medium length; hooked downward about 80°; with long, narrow base. Prickles—few; color—copper. Hairs—none.

I claim:

A new and distinct variety of rose plant of the hybrid tea class, substantially as herein shown and described; characterized particularly as to novelty by the unique combination of clean and healthy foliage, good resistance to fungi diseases, including mildew and blackspot, pointed buds of Deep Canary Yellow color having their upper one-third copper-toned or nearly Oxblood Red as the calyx breaks, said copper and red color tones gradually disappearing as the flowers develop from tight buds to partly open buds, and thereafter the flowers holding a Deep Canary Yellow color until the petals fall, and good lasting qualities of the flowers both on the bush and as cut flowers.

No references cited.